United States Patent [19]

Johnson

[11] Patent Number: 4,746,292
[45] Date of Patent: May 24, 1988

[54] TOOL AND METHOD FOR REMOVING A PARTED ENDODONTIC FILE

[76] Inventor: William B. Johnson, 4254 E. 78th St., Tulsa, Okla. 74136

[21] Appl. No.: 33,251

[22] Filed: Apr. 2, 1987

[51] Int. Cl.$^4$ ............................................. A61C 3/00
[52] U.S. Cl. .................................... 433/141; 433/224
[58] Field of Search ...................... 433/102, 141, 224

[56] References Cited

U.S. PATENT DOCUMENTS

| | | | |
|---|---|---|---|
| 3,322,124 | 5/1967 | Ireland | 433/141 |
| 3,468,031 | 9/1969 | Mumaw | 633/141 |
| 4,247,285 | 1/1981 | Roig-Greene | 433/161 |

Primary Examiner—Robert Peshock
Attorney, Agent, or Firm—Head & Johnson

[57] ABSTRACT

A tool for removing a parted endodontic file from the root canal of a tooth in which a portion of the length of the file is exposed, the tool being in the form of an elongated tubular shaft, the interior diameter of which is slightly greater than the exterior diameter of the file, the tubular shaft having an enlarged handle portion at the proximal end and a vent so that liquid adhesive may be applied to the distal end, the adhesive being drawn by capillary action into the tube adjacent the distal end. The shaft distal end may then be positioned over the exposed portion of a file and retained until the liquid adhesive solidifies. Thereafter, the shaft and parted file may be removed as a unit.

6 Claims, 2 Drawing Sheets

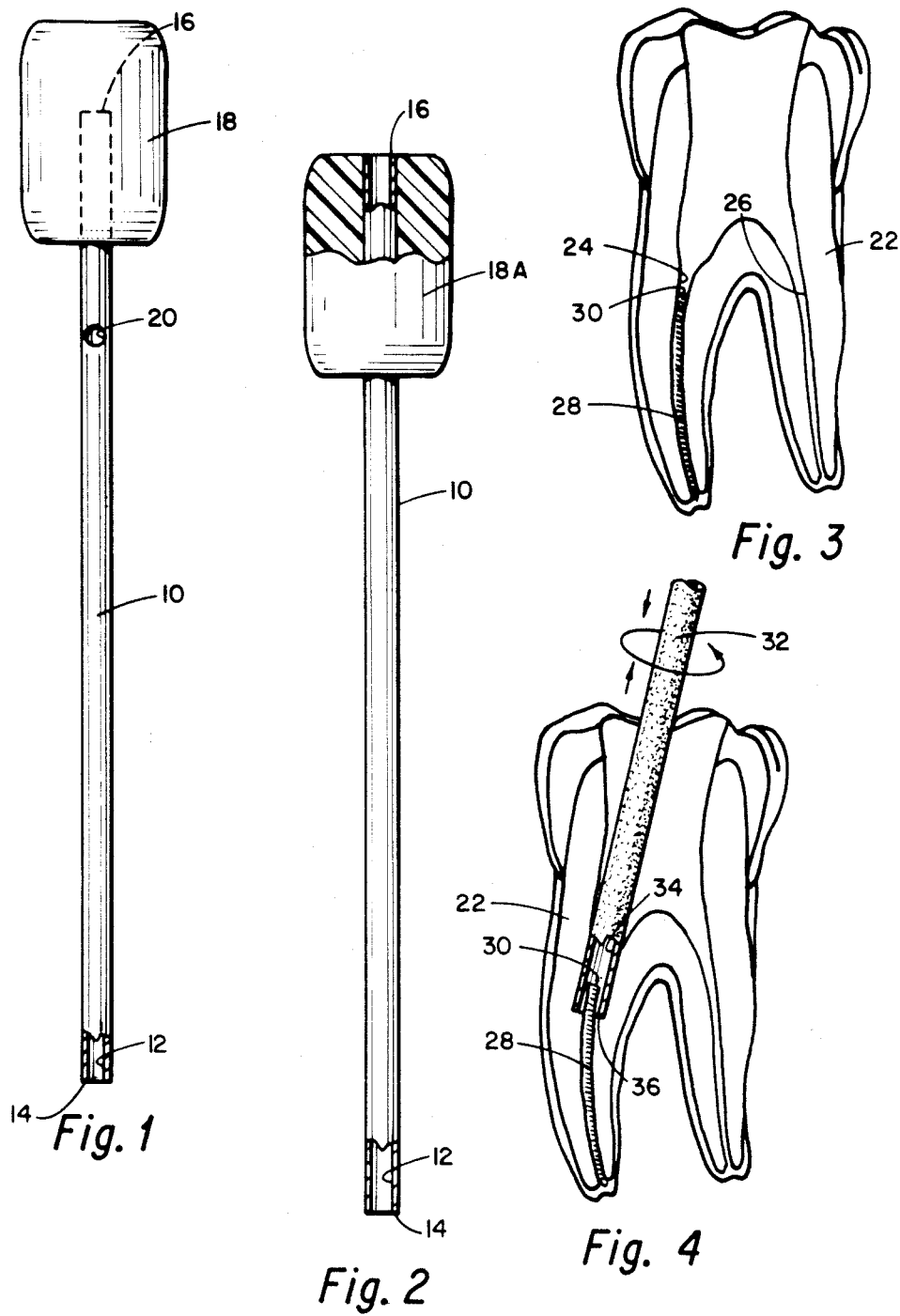

TOOL AND METHOD FOR REMOVING A PARTED ENDODONTIC FILE

SUMMARY OF THE INVENTION

In the practice of endodontics, slender files are used to remove the nerve and pulp of the root canal of a tooth. These files are manufactured in a variety of diameters to accommodate the variance of root canals. Inasmuch as root canals are seldom straight, these files are required to bend as they are utilized. The bending combined with the work of the filing effort can result in the file breaking. If the file break point occurs in the root canal, it cannot be readily removed by pliers or forceps. One method of retrieving a file that has parted within the root canal is to employ a file recovery device which incorporates a threaded rod within a tube. The tube is slipped over the end of the file and the rod is screwed down into the opening of the tube to establish a squeeze grip on the file between the tube and the inner rod. This method has certain undesirable characteristics. One is that the extension process of the rod traveling down the tube often pushes the file out of the tube. A second problem is that the gripping action on the file is often not sufficient to withstand the combined tension and torsional forces which must be applied to extract the parted file. A third problem is the gripping action distorts and weakens softer metals, i.e., silver points. The present invention overcomes these problems.

The present invention is a tool formed of a tubular shaft with a handle and a vent hole. The shaft may be manufactured in a variety of inner diameters to correspond with the standard outer diameters of separated files. The outer diameter of the shaft should be of minimal diameter so as to be able to fit into root canals. A vent hole is provided in the shaft to allow the flow of liquid adhesive by capillary action. This vent may be supplied by having the tube extend through the handle. The handle attached to the tube may be of any suitable size and configuration which can fit conveniently into a patient's mouth and be suitable for applying combined tension and torsional forces.

A glue is used with the tool. The most suitable glue found to date is the formulation that has been given the trade name of "Super Glue" as manufactured by Woodhill Chemical Sales Corporation, Cleveland, Ohio. However, this technique is not limited to the employment of Super Glue; any suitable liquid bonding agent with similar fast setting and high strength characteristics may be employed.

The method of this invention is to first clear a circumferential void around the parted file such as by use of a trepan burr so that the tubular extractor shaft may be slipped over the file. The distance that the shaft must be slipped over the file is a function of the shear strength of the glue bond and the resistance offered by the file. A drop of liquid adhesive is placed in the open end of the shaft and is drawn into a portion of the shaft by capillary action. The shaft is then placed over the exposed extremity of the file and the adhesive allowed to solidify. When the adhesive has reached full bond strength the file is retracted by applying a torque opposite to the shank helix combined with a tension force.

The invention will be better understood by reference to the following description and claims taken in conjunction with the attached drawings.

DESCRIPTION OF THE DRAWINGS

FIG. 1 is an elevational view (with the distal end portion shown broken away and in cross-section) of an elongated shaft and handle formimg the tool of this invention for removing a parted endodontic file.

FIG. 2 is an elevational view as shown in FIG. 1 of an alternate embodiment of the invention. In FIG. 2 the tubular shaft extends through the handle providing venting means to that liquid adhesive applied to the distal end of the shaft will be drawn into the tubular shaft by capillary action. FIGS. 1 and 2 show the tool of the invention greatly enlarged as the tool must be of a small size so as to fit conveniently in the mouth of a patient.

FIG. 3 is a cross-sectional view of a tooth in which a file has been parted, that is, broken, in one of the root canals of the tooth and showing the typical situation in which the tool and the method of this invention are used for removing the parted endodontic file.

FIG. 4 is a cross-sectional view of the tooth of FIG. 3 and showing the use of a rotary trepan burr to expose a portion of the parted file in the area adjacent the part.

DESCRIPTION OF THE PREFERRED EMBODIMENT

Figure 7:
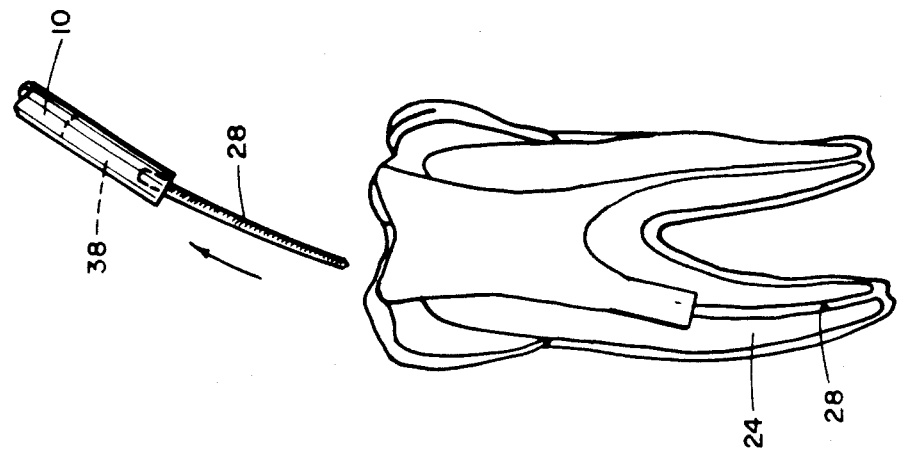
FIG. 7 shows the final step in the method of this invention showing the tooth with the distal end portion of the shaft and the parted endodontic file being removed as a unit from the tooth.

FIG. 1 shows an embodiment of the tool for removing a parted endodontic file of this invention. The tool consists of an elongated shaft 10 which is tubular. That is, it has a central passageway 12. In the simplest embodiment the entire length of the shaft 10 is tubular, however, the only portion which is required to be tubular is that which is adjacent the distal end 14. In the embodiment of FIG. 1 the shaft proximal end 16 is occluded by a handle 18. The handle 18 is preferably cylindrical and of a diameter larger than shaft 10. Handle 18 may be formed integrally with the shaft 10 but in the preferred embodiment the handle 18 is of plastic and secured to the shaft at the proximal end 16.

The passageway 12 within shaft 10 must be of an internal diameter sufficiently large to telescopically receive the end of a parted file as will be pointed out subsequently. The external diameter of shaft 10 should be that which is the minimum necessary to sustain rotational torque and tension as is required to extract a parted file. Shaft 10 is preferably formed of metal, such as stainless steel.

In the use of the tool of FIG. 1, as will be explained in more detail subsequently, liquid adhesive is applied to the distal end 14. Adhesive must extend for a short distance internally of the shaft within the passageway 12 and this can be accomplished easily by the capillary action of the tubular shaft when the distal end 14 is exposed to liquid adhesive as long as the liquid adhesive is not too viscous and as long as air pressure is equalized within the passageway 12. This is accomplished in FIG. 1 by the provision of a vent opening 20 which communicates the interior passageway 12 with the exterior. The vent can be placed at any position on the shaft spaced away from the distal end 14 at least the length of the passageway to be filled with adhesive, but in the preferred arrangement the vent 20 is adjacent handle 18 as illustrated.

FIG. 2 shows an alternate embodiment of the invention; the only difference, being the means of providing a vent to the interior of the tubular shaft 10. Instead of the use of a vent hole, handle 18A is located such that the proximal end 18 of the tubular shaft is exposed so that vent is achieved through the proximal end. The embodiments of FIGS. 1 and 2 function substantially identically and differs only in the means of providing a vent to the interior passageway 12.

Figure 5:
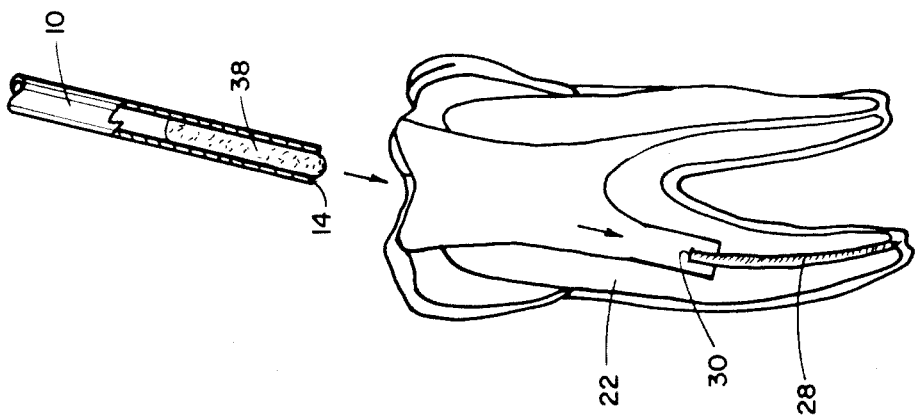
FIG. 5 shows the tooth as in FIGS. 3 and 4 with a portion of the parted endodontic file exposed adjacent the parted end and showing the distal end of the tool of this invention as it is being inserted into the tooth. The distal end has liquid adhesive therein.

The method of using the tool of FIGS. 1 and 2 will be next described with reference to FIGS. 3 through 7. FIG. 3 illustrates a typical tooth 22 having root canals 24 and 26. Root canal 24 shows a parted endodontic file 28 therein. As stated previously, in removing the nerve and pulp of a root canal the file may part primarily as a consequence of rotational torque applied above the torsional limit. This is particularly true when the root canal is curved since increased rotational resistance is imparted to the file. In some instances the file 18 will part so that the end 30 is exposed, that is, where the tooth structure is not closely surrounding the parted end 30. In such a situation, the file can be removed by pliers or forceps. In other cases the part takes place in an area wherein the tooth structures completely surrounds the parted end portion of the file. In such situations it is first necessary to expose a short length of the file adjacent the end 30. FIG. 4 shows a means whereby this is accomplished. A rotary trepan burr 32 is applied to the tooth. The trepan burr 32 has a tubular opening 34 therein adjacent the burr end 36 which is placed in axial alignment with the file 28 at the parted end 30. Rotational energy is applied to burr 32 to drill away the tooth structure which surrounds the file adjacent the parted end 30. FIG. 5 shows the tooth 22 after the use of the trepan burr showing that the portion of the file 28 adjacent the parted end 30 is exposed.

The next step in the practice of the invention is to employ a tool as in FIGS. 1 or 2. A drop of liquid adhesive, such as Super Glue, or any equivalent fast setting, high strength, low viscosity liquid adhesive is applied to the distal end 14 of the tubular shaft 12 and, by capillary action, a portion of the adhesive is drawn into the shaft adjacent the distal end 14, the liquid adhesive being indicated by the numeral 38. With the liquid adhesive therein, the shaft 10 is positioned so that the distal end portion 14 telescopically extends over the exposed portion of file 28 adjacent the parted end 30. This permits the liquid adhesive 38 to completely surround the file 28 adjacent the parted end 30.

Figure 6:
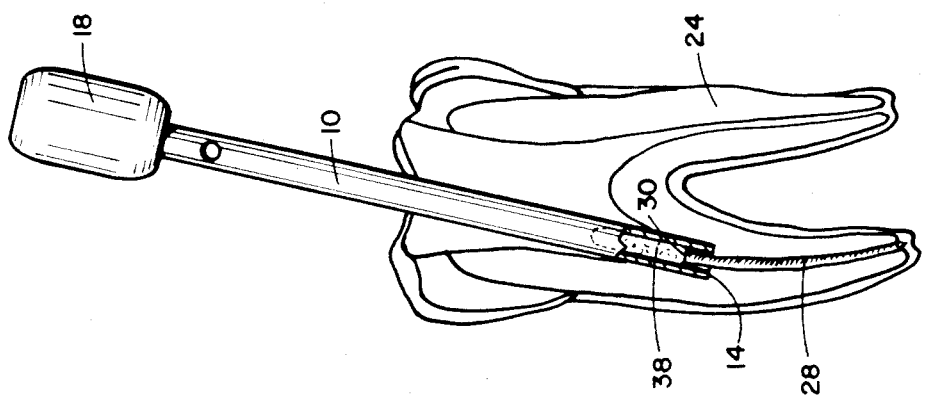
FIG. 6 shows the tool of this invention in position with relation to a tooth and showing the distal end of the shaft positioned telescopically over the exposed end of the endodontic file with the adhesive surrounding the exposed end. The tool is retained in the position as shown in FIG. 6 until the adhesive sets or solidifies.

The shaft 10 is maintained in the position as shown in FIG. 6 until the adhesive sets. By properly selecting the correct adhesive the waiting time can be relatively short. As the adhesive solidifies the parted file 28 and shaft 10 are bonded into a single unit. Thereafter, by the application of tension and rotational torque, the parted file 28 can be removed as shown in FIG. 7. It is important that the adhesive bond sufficiently to permit the transfer of rotational torque from the tubular shaft 10 to the parted file 28 since the typical endodontic file has the cuttings thereon arranged in a conical configuration and by the proper direction of rotation of the shaft and thereby the file, the file is more or less unthreaded from within the root canal.

The length of the parted file 28, which must be exposed at the parted end 30, will depend upon how tenaciously the parted file is lodged within the tooth and if one trial of the tool results in the adhesive failing to secure sufficiently with the file to transmit rotational torque necessary to dislodge the file the step 4, 5 and 6 may be repeated, exposing a greater length of the file adjacent the parted end 30 until a sufficiently long portion of the file is exposed to transmit the necessary rotational torque and tension to the file to secure its removal.

The tool of FIGS. 1 or 2 is intended for a single time use and since they are relatively small and made of readily available components, the tool is not expensive.

The method of this invention is very simply practiced without requiring a great deal of time to learn the technique. It does not require the mechanical attachment of one element to another as in some of the methods presently employed. Further, it does not require the intricate manipulation of mechanisms within the confines of the mouth of the patient.

While the drawings show shaft 10 as beeing straight, the tool is not so limited and may be bent or curved to make it easier for the dentist to use.

While the invention has been described as it particularly applies to the removal of parted file, it can be seen that the same technique can be used for removing silver cones used for endodontic fillngs.

The claims in the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A tool for removing a parted endodontic file from the root canal of a tooth in which a portion of the length of the file adjacent the part is exposed comprising:

an elongated tubular shaft having a proximal end and a distal end and having an internal diameter at least in the area at said proximal end greater than the exterior diameter of the exposed portion of the file to be removed whereby the shaft proximal end may be extended over the parted file to telescopically receive the exposed end portion of the parted file therein;

an enlarged diameter handle portion secured to said shaft at said proximal end; and vent means spaced from said distal end of said shaft communicating the interior of said shaft with the exterior whereby a liquid adhesive may be applied to said shaft distal end and in which the adhesive will be drawn into said shaft by capillary action.

2. A tool for removing a parted endodontic file from a root canal according to claim 1 wherein said shaft is of metal and said handle is of non-metallic material.

3. A tool for removing a parted endodontic file from a root canal according to claim 1 wherein said interior of said shaft is closed adjacent said proximal end, such as by a handle, and wherein said tubular shaft has an opening therein communicating with the shaft interior, the opening being spaced from said shaft distal end.

4. A tool for removing a parted endodontic file from a root canal according to claim 1 wherein said tubular shaft is exposed at said proximal end to provide an uninterrupted internal passageway through said shaft from the distal to the proximal end, the exposed internal passageway at said shaft proximal end providing said vent means.

5. A method of removing a parted endodontic file from the root canal of a tooth in which a portion of the length of the file adjacent the part is exposed, comprising the steps of:

applying quick setting liquid adhesive to the distal end of an elongated tubular shaft so that a quantity of liquid adhesive is drawn into the tubular shaft at the distal end by capillary action;

positioning the distal end of the tubular shaft over the exposed portion of the endodontic file so that the exposed portion of the file is surrounded by liquid adhesive;

retaining the shaft within the exposed end of the endodontic file received therein until the adhesive solidifies; and applying pulling tension and torsional forces on the proximal end of the tubular shaft to remove the shaft and the parted file as a bonded unit.

6. A method of removing a parted endodontic file from the root canal of a tooth comprising the steps of:

applying a tubular trepan burr to the tooth with the file in axial alignment with the burr tubular passageway;

rotating the trepan burr to remove tooth material along the exterior of the parted file for a selected length to expose a portion of the parted file adjacent the parted end;

applying quick setting liquid adhesive to the distal end of an elongated tubular shaft so that a quantity of liquid adhesive is drawn into the tubular shaft at the distal end by capillary action;

positioning the distal end of the tubular shaft over the exposed portion of the endodontic file so that the exposed portion of the file is surrounded by liquid adhesive;

retaining the shaft within the exposed end of the endodontic file received therein until the adhesive solidifies; and applying pulling tension and rotational forces on the proximal end of the tubular shaft to remove the shaft and the parted file as a bonded unit.

* * * * *